(12) United States Patent
Hendriks et al.

(10) Patent No.: US 9,179,985 B2
(45) Date of Patent: Nov. 10, 2015

(54) BIOPSY GUIDANCE BY ELECTROMAGNETIC TRACKING AND PHOTONIC NEEDLE

(75) Inventors: Bernardus Hendrikus Wilhelmus Hendriks, Eindhoven (NL); Guy Shechter, Briarcliff Manor, NY (US); Drazenko Babic, Eindhoven (NL); Wim Crooijmans, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 448 days.

(21) Appl. No.: 12/867,267

(22) PCT Filed: Feb. 27, 2009

(86) PCT No.: PCT/IB2009/050793
§ 371 (c)(1),
(2), (4) Date: Aug. 12, 2010

(87) PCT Pub. No.: WO2009/109879
PCT Pub. Date: Sep. 11, 2009

(65) Prior Publication Data
US 2010/0317964 A1     Dec. 16, 2010

Related U.S. Application Data

(60) Provisional application No. 61/033,056, filed on Mar. 3, 2008, provisional application No. 61/058,941, filed on Jun. 5, 2008.

(51) Int. Cl.
*A61B 5/06* (2006.01)
*A61B 19/00* (2006.01)
(Continued)

(52) U.S. Cl.
CPC ........... *A61B 19/5244* (2013.01); *A61B 5/0075* (2013.01); *A61B 5/0084* (2013.01); *A61B 5/6848* (2013.01); *A61B 5/0066* (2013.01); *A61B 10/0275* (2013.01); *A61B 10/04* (2013.01); *A61B 17/3403* (2013.01); *A61B 17/3421* (2013.01);
(Continued)

(58) Field of Classification Search
CPC .. A61B 5/0075; A61B 5/0084; A61B 5/6848; A61B 5/0066; A61B 19/5244; A61B 10/0275; A61B 10/04; A61B 2019/5276; A61B 2019/5251; A61B 2019/5206; A61B 2017/00061; A61B 2017/00066; A61B 2576/00
USPC .................... 382/128, 130–131; 600/424, 567
See application file for complete search history.

(56) References Cited

U.S. PATENT DOCUMENTS 5,318,023 A      6/1994  Vari et al.
5,823,958 A  * 10/1998  Truppe ......................... 600/426
(Continued)

FOREIGN PATENT DOCUMENTS

JP      2001524339     12/2001
JP      2005118134      5/2005
(Continued)

*Primary Examiner* — Long V Le
*Assistant Examiner* — Angela M Hoffa

(57) ABSTRACT

A system for providing integrated guidance for positioning a needle in a body has two levels of guidance: a coarse guidance and a fine guidance. The system includes a non-invasive tracking system for tracing the biopsy device in the body, for providing the coarse guidance. Furthermore, the system includes an optical detector mounted on the needle for obtaining optical information discriminating tissue in the body, for providing the fine guidance.

20 Claims, 4 Drawing Sheets

(51) Int. Cl.
  *A61B 10/04*   (2006.01)
  *A61B 5/00*    (2006.01)
  *A61B 10/02*   (2006.01)
  *A61B 17/34*   (2006.01)
  *A61B 17/00*   (2006.01)

(52) U.S. Cl.
  CPC ............... *A61B 2017/00061* (2013.01); *A61B 2017/00066* (2013.01); *A61B 2019/5206* (2013.01); *A61B 2019/5251* (2013.01); *A61B 2019/5276* (2013.01); *A61B 2576/00* (2013.01)

(56) References Cited

U.S. PATENT DOCUMENTS

| | | | |
|---|---|---|---|
| 6,006,750 A | 12/1999 | Field | |
| 6,135,946 A * | 10/2000 | Konen et al. | 600/117 |
| 6,233,476 B1 | 5/2001 | Strommer et al. | |
| 6,293,911 B1 * | 9/2001 | Imaizumi et al. | 600/160 |
| 6,445,943 B1 * | 9/2002 | Ferre et al. | 600/424 |
| 6,564,087 B1 | 5/2003 | Pitris et al. | |
| 6,687,531 B1 * | 2/2004 | Ferre et al. | 600/424 |
| 6,694,167 B1 * | 2/2004 | Ferre et al. | 600/424 |
| 6,785,571 B2 | 8/2004 | Glossop | |
| 6,826,424 B1 * | 11/2004 | Zeng et al. | 600/476 |
| 6,898,458 B2 * | 5/2005 | Zeng et al. | 600/476 |
| 7,115,841 B2 * | 10/2006 | Zeng et al. | 219/476 |
| 7,190,452 B2 * | 3/2007 | Zeng et al. | 356/326 |
| 7,253,894 B2 * | 8/2007 | Zeng et al. | 356/326 |
| 7,603,161 B2 * | 10/2009 | Wurmfeld et al. | 600/424 |
| 7,753,852 B2 | 7/2010 | Maschke | |
| 7,769,426 B2 | 8/2010 | Hibner et al. | |
| 7,826,883 B2 * | 11/2010 | Hibner et al. | 600/407 |
| 7,840,251 B2 * | 11/2010 | Glossop | 600/424 |
| 2005/0154277 A1 | 7/2005 | Tang et al. | |
| 2005/0182295 A1 * | 8/2005 | Soper et al. | 600/117 |
| 2005/0261568 A1 | 11/2005 | Hular et al. | |
| 2006/0281971 A1 * | 12/2006 | Sauer et al. | 600/109 |
| 2007/0032723 A1 | 2/2007 | Glossop | |
| 2007/0078334 A1 | 4/2007 | Scully et al. | |
| 2008/0125634 A1 * | 5/2008 | Ryan et al. | 600/342 |
| 2008/0292164 A1 * | 11/2008 | Azar et al. | 382/131 |
| 2009/0326385 A1 * | 12/2009 | Hendriks et al. | 600/478 |
| 2010/0331782 A1 * | 12/2010 | Hendriks et al. | 604/164.12 |
| 2011/0009772 A1 * | 1/2011 | Braun et al. | 600/562 |
| 2011/0218445 A1 * | 9/2011 | Braun et al. | 600/478 |
| 2011/0251494 A1 * | 10/2011 | Hendriks et al. | 600/478 |
| 2011/0270093 A1 * | 11/2011 | Desjardins et al. | 600/476 |

FOREIGN PATENT DOCUMENTS

| | | |
|---|---|---|
| JP | 2006006919 | 1/2006 |
| WO | WO9943253 | 9/1999 |
| WO | WO03020119 | 3/2003 |
| WO | WO2006095343 | 9/2006 |
| WO | WO2007083310 | 7/2007 |
| WO | WO2007147058 | 12/2007 |

\* cited by examiner

BIOPSY GUIDANCE BY ELECTROMAGNETIC TRACKING AND PHOTONIC NEEDLE

CROSS REFERENCE TO RELATED CASES

Applicants claim the benefit of International Application Number PCT/IB2009/050793, filed Feb. 27, 2009, and U.S. Provisional Applications Ser. Nos. 61/033,056, filed Mar. 3, 2008, and 61/058,941, filed Jun. 5, 2008. A related application is PCT/IB2009/050752, filed Feb. 25, 2009 (published as WO2009109873-A1, Sep. 11, 2009), "Biopsy Guidance by Image-Based X-Ray Guidance System and Photonic Needle", which has entered the U.S. national stage as U.S. application Ser. No. 12/919,220, filed Aug. 25, 2010.

FIELD OF THE INVENTION

The present invention relates to a system for integrated guidance for positioning a biopsy device in a body, to a biopsy device and to a method for positioning a biopsy device.

BACKGROUND OF THE INVENTION

For correct diagnosis of various cancer diseases biopsies are taken. This can either be done via a lumen of an endoscope or via needle and catheter biopsies. An example of a needle biopsy is shown in FIG. 1, where a biopsy is taken from the prostate via the rectum. In order to find the correct position to take the biopsy, various imaging modalities are used such as X-ray, CT, MRI and ultrasound. In case of prostate cancer in most cases the biopsy is guided by ultrasound (see FIG. 1). Although helpful, these methods of guidance are far from optimal.

There are problems directly related to the biopsy:

The resolution of the imaging system is limited and, furthermore, these imaging modalities cannot in most cases discriminate normal and neoplastic tissue and further differentiate between benign and malignant tissue.

As a result of that, there is a high level of uncertainty whether an appropriate tissue specimen is taken.

In addition to that, the biopsies are often taken blindly, with limited feedback of where the needle is relative to the target tumor, which leads to an additional uncertainty whether the lesion has been hit by the needle. It is clear that guidance improvement is required to target the biopsy needle to the correct position in the tissue.

A way to solve the navigation towards the suspicious tissue is by navigating the biopsy needle tip by employing electromagnetic guidance as described in U.S. Pat. No. 6,785,571 B2. However the accuracy of the method is limited to a few millimeters. As a result for small sized suspicious tissue volumes there is a certain chance of taking the biopsy at the wrong place. A further limitation is that even if one could guide the biopsy needle to the exact location corresponding to the pre-recorded image, one is never sure that this is the exact location due to the compressibility of the tissue. Due to the force of the biopsy needle on the tissue during advancement, the tissue may become deformed.

If the specimen taken appears to be cancerous, in most cases this cancerous tissue will be removed by surgery (especially when the tumor is well localized) or treated percutaneously using RF, microwave, or cryoablation.

The surgical approach is confounded by the fact that the surgeons typically use only their eyes and hands (palpation) to find the tumor and have to rely on the information of pre-recorded images. These pre-recorded images provide information on the position of the tumor but do not always clearly show the tumor boundaries. Sometimes, the surgeon implants a marker under image guidance, providing him or her with a reference point to focus on during the surgical procedure. Again guiding the localization wire to the correct position is difficult.

It is particularly difficult to find the boundaries of the tumor, in fact it is virtually impossible. As a result of that, the surgeon removes a significant amount of tissue around the core of the tumor to make sure that the entire tumor mass is removed. Although removing an additional amount of tissue around the tumor will indeed lead in most cases to complete removal, the surgeon is never sure. The number of recurrences of the cancer after removal is 30%, which indicates that some parts of the tumor remained in place and caused further tumor re-growth. One could of course increase the amount of tissue to be removed but this in several cases difficult. In some cases vital structure are present in the tissue (nerves, important blood vessels, brain tissue). The surgeon has then to decide whether the malfunctioning due to the removal of additional healthy tissue outweighs the risk of not completely removing the tumor. It is important to note that when resection is not complete, the surgeon has, in fact, cut through the tumor and may cause further dissemination of the tumor.

The biopsy device may also be used as a device for administering drugs or a therapy (like ablation) at a certain position in the body without removing tissue, for instance for injecting a fluid at the correct location of the affected body part. The same drawbacks apply for these interventions where it is difficult to guide the biopsy device to the correct location.

The current way of working to take a biopsy has some drawbacks, including:
  difficult to guide the biopsy needle to a centre of the tissue to be investigated;
  difficult to delineate the tumor boundaries (shape and size of tumor); and
  taking specimen out of the body for the histological analysis may cause further dissemination of the tumor.

SUMMARY OF THE INVENTION

It is an object of the invention to mitigate one or more of the above mentioned drawbacks.

This is achieved by the subject matter of the respective independent claims. Further exemplary embodiments are described in the respective dependent claims.

Generally, a system for integrated guidance for positioning a biopsy device in a body according to the invention, comprises a tracking device for coarse guidance, an analyze device for fine guidance, comprising an optical detector and providing information discriminating tissue of the body, and a biopsy device. The biopsy device is adapted to be traced by the tracking device, and the optical detector is integrated in the leading portion of the biopsy device.

In other words, the invention provides an integrated system that comprises an apparatus insertable into an anatomical body, said apparatus comprises an insertable portion for holding a position sensor that can transmit a signal indicative of its position in a frame of reference, wherein the insertable portion contains an optical fiber for detecting optical properties of tissue in front of the insertable portion with an optical modality; wherein the optical properties are used to assure that the insertable portion is located in suspicious tissue i.e. to fine position the insertable portion in the targeted tissue.

The biopsy device or the insertable portion might be a biopsy needle or might be a canula, trocar or catheter adapted to receive a needle by which the biopsy is actually performed.

According to an exemplary embodiment, the system has means for computing a registration of images to the position sensor held in the insertable portion of the anatomical body.

The imaging modality may be one of reflectance spectroscopy, fluorescence spectroscopy, autofluorescence spectroscopy, differential path length spectroscopy, Raman spectroscopy, optical coherence tomography, light scattering spectroscopy, or multi-photon fluorescence spectroscopy.

Preferably, the optical information is registered into the pre-recorded image taken by an non-invasive imaging modality (X-ray, CT, MRI, Ultrasound) by making use of the location identified by the position sensor in the frame of reference that in turn is registered to a position in the pre-recorded image.

Preferably, the needle navigation system provides the needle position with respect to pre-recorded images, all of which is coupled to the optical information obtained by the needle, characterized in that the navigation system provides the coarse guidance, while the optical information provides the final precise guidance to the biopsy location.

The reflectance spectra of different types of tissue are in general different due to the different molecular constitution of the tissues. As a result of measuring these spectra, it is possible to distinguish different tissues from each other. The fact that the optical method has only a limited penetration depth, the imaging depth is only a few centimeters. Guiding the needle without the guidance of the non-invasive modality is difficult because there is no overview where the needle is in space. Furthermore, without being able to register the optical information to the position of the needle inside the patient means that as soon as the needle is moved the previous measured data has lost its relevance.

Another aspect of the invention is that in translating the measured optical data into a tissue type can be difficult when no information about the surrounding morphology is known. Hence the decision making of the tissue characterization improves having the morphology information coming from the non-invasive imaging system as input. Hence preferably first the optical data is registered to the non-invasive imaging data, then the optical information together with the morphology information around the needle coming from the non-invasive imaging modality is used in translating the measured optical data into a tissue type in front of or near the needle. For instance when the needle is in soft tissue the optical information can be affected whether a bone structure is close by or not. Taking this into account a more reliable tissue characterization is possible.

Below is a short summary of advantages of the system of the invention:

the system is able to interactively follow the biopsy needle from the incision to the target point by electromagnetic needle navigation on medical images and provide molecular tissue information at every point along the needle trajectory.

the region along the needle trajectory can be optically scanned (scan forward and scan aside) in order to provide indications on lesion existence at the molecular level.

tumor boundaries deduced from needle scanning and from pre-recorded images (X-ray, Ultrasound, MRI) are compared. For instance the X-ray information gives an estimate of the shape of the tumor (see FIG. 8), but the exact boundary cannot be determined. The needle gives detailed information of the tumor boundary but this information is only obtained along the needle trajectory. Combining the X-ray shape of the tumor with the 1 dimensional information of the needle a new estimate of the 3D tumor size can be calculated (see embodiment 4). The newly deduced enlarged boundary will be a better estimate for the tumor boundary.

biopsy needle is used to do the fine positioning of the localization wire, the electromagnetic navigation the coarse localization. The localization wire containing fixation means and may be equipped with a fiber.

BRIEF DESCRIPTION OF THE DRAWING

In the following, the invention will be described by way of exemplary embodiments with respect to the attached drawing.

DETAILED EMBODIMENTS OF THE INVENTION

Figure 1:
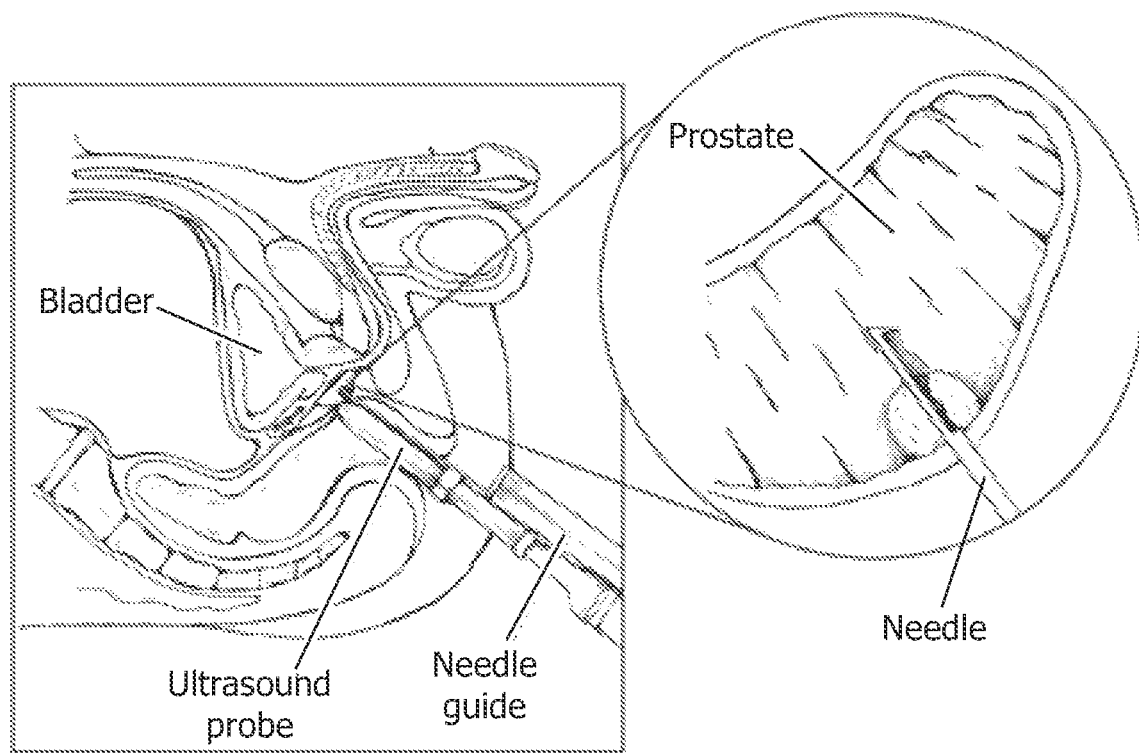
FIG. 1: schematic drawing of taken a biopsy via the rectum under ultrasound guidance.
Figure 2:
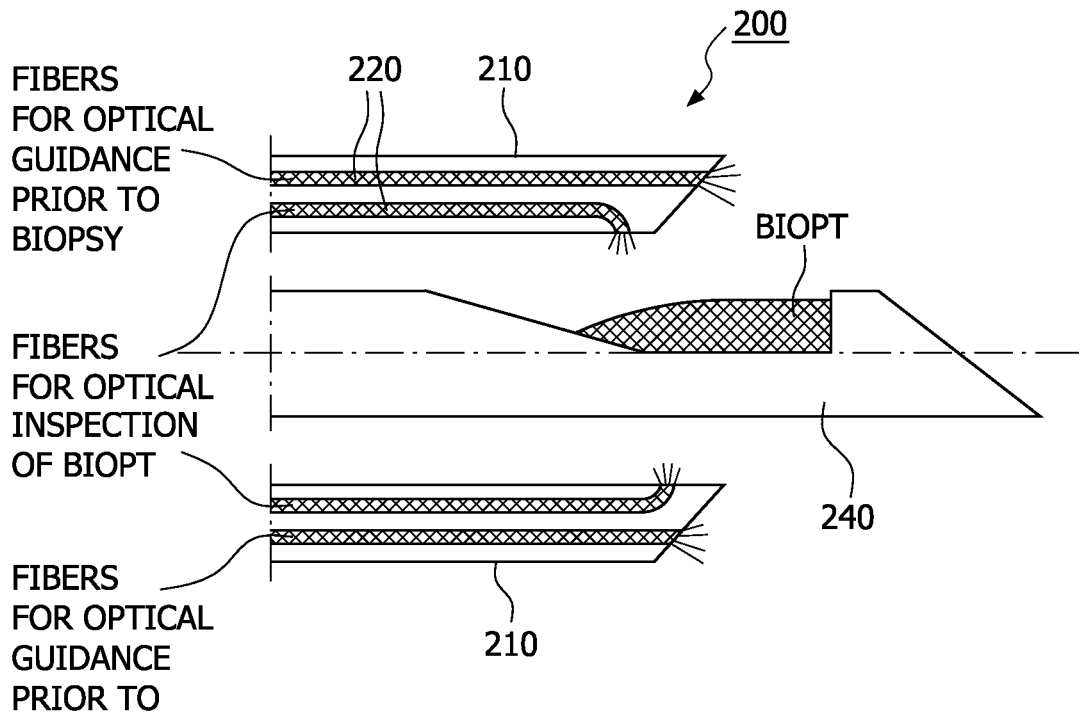
FIG. 2: cross section of an embodiment, in which the optical fibers for guidance of biopsy and inspection of biopsy are integrated in the shaft.

The first embodiment is based on a needle navigation based needle guidance system as described in U.S. Pat. No. 6,785,571. Furthermore, the shaft 210 of the biopsy device 200 contains a fiber 220 or fiber bundle (see FIG. 2). Further, the shaft 210 is adapted to accommodate a needle 240 for taking a biopt. Preferably, the fiber bundle 220 is located in the shaft 210 such that the respective ends of the fibers are located in the tip portion of the biopsy device. In other words, some of the fibers might end in the front surface of the biopsy device, and/or some of the fibers might end in the vicinity of the front surface at the side surface or wall surface of the biopsy device. Furthermore, there could be some fiber ends orientated in the direction to a biopt harvested by the biopsy device, and some other fiber ends orientated in the direction to the front or the side of the biopsy device, for optical guidance prior to biopsy.

It is noted, that any fiber might be used to emit and/or to receive light.

Figure 3:
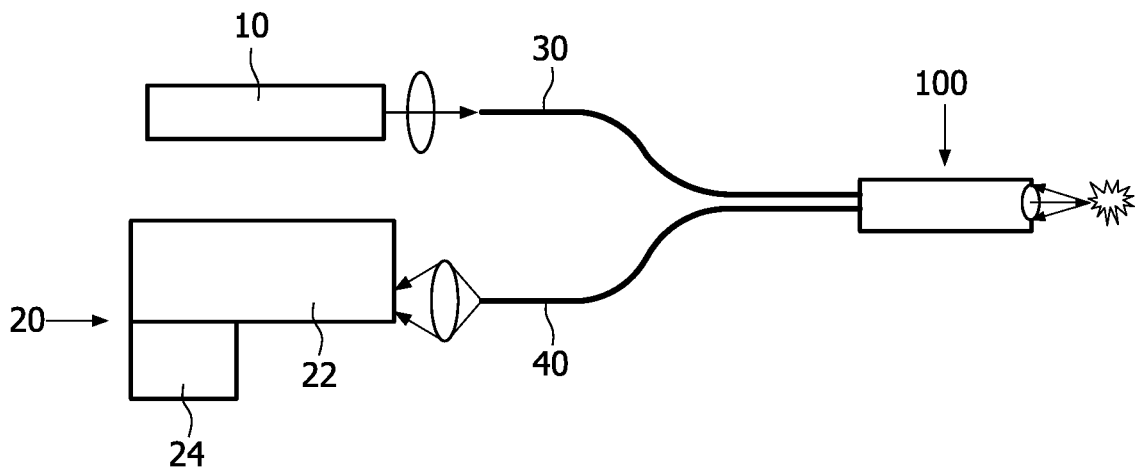
FIG. 3: set-up for Raman or fluorescence spectroscopy.

Further components of the system are shown in FIG. 3. According to this embodiment, some of the fibers 30 are coupled to a light source 10 outside the body and are used for excitation of the tissue in front of the shaft tip of the biopsy device 100. Part of the scattered and emitted light is collected by other fibers 40 and guided to a detector including a spectrograph 22 and a CCD-camera, where for instance an autofluorescence or Raman spectrum is recorded (see FIG. 3). Upon inspection of the spectrum it is decided to either take a biopsy or to move the shaft further to another position if no anomalies in the spectrum are found.

During the insertion of the biopsy device in the tissue, spectra are recorded and linked to the position of the biopsy device deduced from the device navigation. In this way for various points information is obtained of the tissue and is combined into for instance in the image obtained by X-ray. The coarse guidance to the diseased tissue is performed by the electromagnetic guidance system. The fine guidance is based on the optical information. When the final location is reached a biopsy is taken. Optionally, the biopsy may be checked optically whether it contains the diseased tissue.

A way to provide real-time tissue characterization is by means of optical methods. For instance optical reflectance spectroscopy or Raman spectroscopy are known to provide signatures that are tissue specific. In the reflectance spectroscopy method where tissue is illuminated with a broad band light source, the reflected scattered spectral light distribution is measured. The difference in tissue properties (i.e. difference in scattering properties of the specific tissue) is visible in the changes of the spectral light distribution compared to the original spectral distribution of the illumination source. Furthermore, optical spectroscopic imaging (i.e. extending the optical imaging from a point measurement to two-dimensional imaging provides even more detailed tissue characterization. In this case tissue is viewed with micron resolution allowing cellular structures to become visible allowing detailed tissue analysis. When this cellular imaging is combined with optical spectroscopy, tissue characterization can be achieved, without using staining, that comes close to what currently is being used in ex-vivo pathology.

Figure 4:
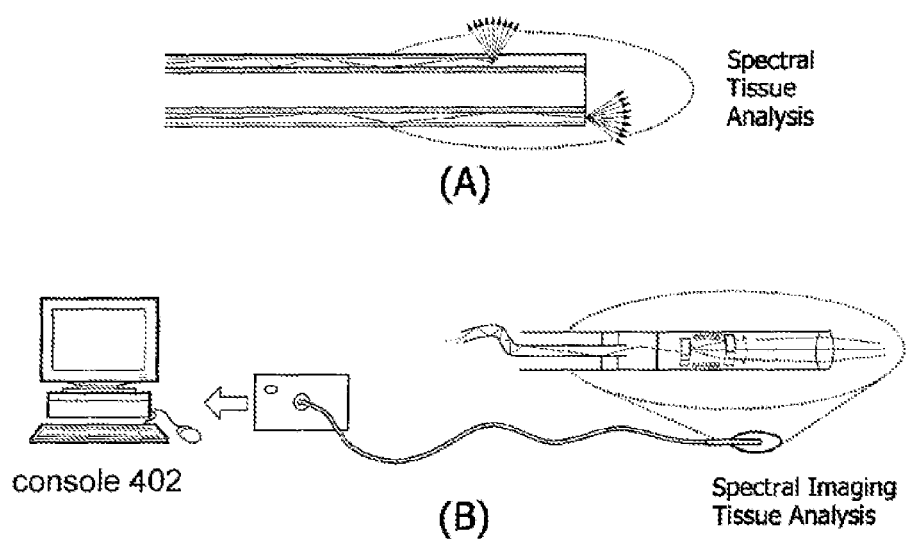
FIG. 4: two types of fiber based needles: (A) fixed fiber and (B) scanning fiber.

To make these methods available in a biopsy device, optical fiber technology is employed. By integrating fibers into the device, optical probing at the tip of the distal end of the fiber at the tip of the biopsy device becomes possible. The analysis can then be done at a console 402 that is attached to the proximal end of the fiber (see FIG. 4). The console is an integral part of the integrated navigation system. Two different types of fiber based needles are envisioned. In the first type the fibers are rigidly integrated into the needle (see FIG. 4(A)) allowing spectroscopic analysis of the tissue near the needle tip. Since the fiber are rigidly incorporated no cellular imaging is possible. In the second type a scanning fiber is integrated into the needle (see FIG. 4(B)). When a lens system is mounted in front of the fiber a scanning confocal microscope is established allowing microscopic imaging of tissue. In order to scan the fiber a motor must be integrated in the needle, making the system more complex than the fixed fiber.

Figure 5:
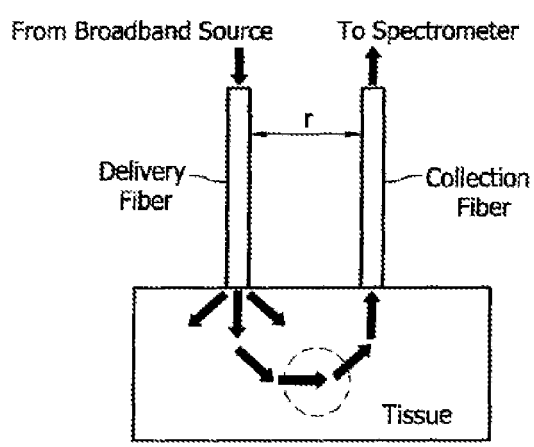
FIG. 5: schematic drawing of the experimental setup for measuring the optical spectra.

There are various optical techniques that can be coupled to these two ways of tissue inspection, where spectroscopy is one of them. An example is optical spectroscopy. The spectroscopic measurement on excised tissue is performed with the needle equipped with optical fibers as is shown in FIG. 5, The light source coupled to the fiber is a broadband light source. The reflectance spectra are measured with a spectrometer.

Figure 6:
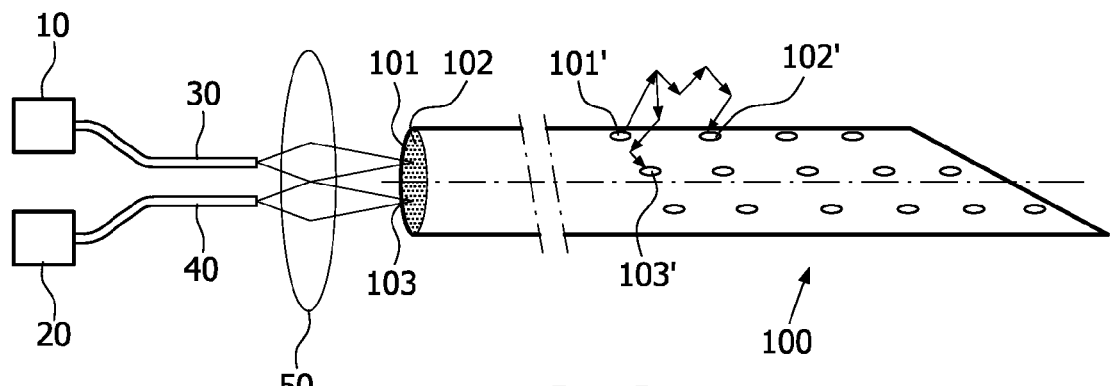
FIG. 6: intelligent biopsy needle.

In a further embodiment the needle contains a collection of optical fibers without having a lumen (see FIG. 6). Each of the fiber entrance positions at the base of the needle (for example in FIG. 6, the positions indicated by numbers 101, 102 and 103) relates to a fiber exit position at the head of the needle (in FIG. 6 indicated by primed numbers 101', 102' and 103'). In this way the needle head is covered with various optical probe positions.

Light is coupled into and out of the optical fibers at the base of the needle. A light source 10, connected to an excitation fiber 30, focused by a lens 50, illuminates for instance fiber 101. The light will cross the fiber and illuminate the tissue around exit position 101'. Light scattering from this position can for instance reach position 102' and 103'. Detector 20 is connected to fiber 40 that collects the light coming from each fiber (101, 102 and 103 respectively) through lens 50. The intensity of the light is a measure for the amount of absorption and scatter between exit positions 101' and 102' and 103'. From these signals the tissue characteristics around the needle can be extracted. It is worth noting that this embodiment allows two-dimensional imaging of scattering and absorption properties of the tissue surrounding the needle, with a lateral resolution equal to that of the fiber-to-fiber distance. Moreover, it is also possible to perform an optical coherence scan for each fiber, which gives for each fiber a depth scan along a line. Combining these lines, it is possible to reconstruct a three-dimensional image of the tissue around the needle, again with a lateral resolution equal to that of the fiber-to-fiber distance.

One other variation of this embodiment is the implementation of fluorescence imaging and/or spectroscopic measurements. In this case source 10 and fiber 30 serve as an excitation fiber, hence to excite the fluorescent molecules and collection fiber to collect the fluorescent light emitted by the molecules. Similar as discussed in the first embodiment it is possible to perform Raman spectroscopy but now in principle for each fiber end position 101', 102', etc.

Finally, it is also possible to perform diffuse optical tomography (DOT) around the needle. This allows functional imaging in a relatively large volume around the needle similar to what is done in optical mammography. In this embodiment one or more fibers are used for (sequential) illumination of the tissue. One or more other fibers are used to collect the scattered light. Using an image reconstruction algorithm it is possible to obtain a 3D map of the optical properties in a region around the needle. The main advantage of DOT is the high penetration depth compared to other optical methods: about half of the source detector distance. The most advantageous wavelength region for DOT is the near infrared (NIR). Here the penetration depth is at it's maximum and the optical properties are strongly determined by important physiologic parameters like blood content and oxygen saturation. By combining DOT at different wavelengths it is possible to translate optical parameters into physiological parameters.

The imaging methods mentioned above can rely on direct absorption and scattering properties of the tissue under investigation, however it is also possible to map fluorescence of tissue, by illuminating with the proper wavelength and simultaneously blocking the illumination wavelength at the detector side. The fluorescence can be endogenous or exogenous, i.e. with the aid of contrast agents. The specificity of the fluorescence detection can be improved by methods well known in the art such as fluorescence lifetime imaging.

A further aspect of the invention is that the tumor boundaries deduced from needle information and that of the information from the x-ray are compared by coupling the position using the electromagnetic navigation information to link the position of the needle to that of the pre-recorded X-ray image.

However, in order to accurately track areas of interest in an anatomical body, it is necessary to rigidly fix the position sensor near or at a location of interest in the anatomical body. It is also necessary to then register the position sensor with the anatomical body. A position sensor is registered to an anatomical body by correlating the position of the position sensor in the anatomical body to the determined position of the position sensor in the frame of reference. At that time, the location of interest in the anatomical body can be tracked in a fixed frame of reference, such as the operating room frame of reference, by determining the position of the position sensor.

Recently, magnetic sensor coils or fiber optic sensors that are reasonably small, and therefore can be substantially unobtrusively inserted into an anatomical body, might be successfully used.

Figure 7:
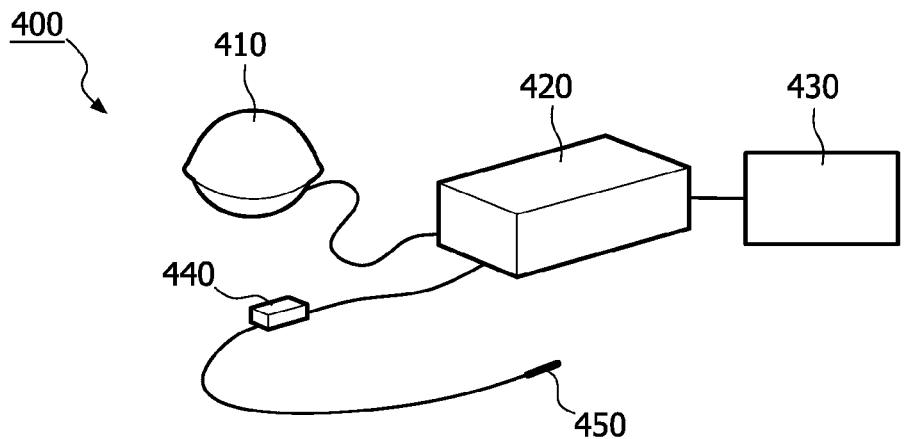
FIG. 7: schematic illustration of an electromagnetic tracking device.

FIG. 7 shows an appropriate position sensor system or tracking device 400, comprising a control unit 420 that is connected to a field generator 410 and a host computer. The host computer can be a user supplied work station 430. The field generator 410 generates a complex electromagnetic field within a frame of reference. A position sensor 450 at the tip of the biopsy device, within the frame of reference can sense the complex electromagnetic field. The position sensor may also be located at another part of the biopsy device, as long as the spatial relation between the tip and the sensor is known. The system 400 also comprises a sensor interface unit 440 that interfaces the control unit 420 to the position sensor 450. It is understood that these components may be integrated together. For example, the sensor interface unit 440 may be combined with the control unit 420.

The position sensor 450 generally comprises a sensor element, such as a magnetic sensor coil, which reacts to, or senses, the complex electromagnetic field generated by the field generator 410. As the position sensor moves in the electromagnetic field generated by the field generator, the sensor coil generates a position signal, that is indicative of the position of the position sensor. Generally, the sensor coil will react to changes to both the position and orientation of the position sensor in the frame of reference. In this way, the position signals, generated by the sensor coil are indicative of both position and orientation of the position sensor. The position signals are received by the sensor interface unit 440 and converted to a form which can be understood by the host computer 430.

Thus, the position and orientation of the position sensor 450 can be determined in the frame of reference of the field generator 410. The frame of reference of the field generator is generally a fixed frame of reference, such as the frame of reference of the operating room. In order for the position sensor to be of assistance in tracking or determining the position and orientation of a location of interest in an anatomical body, it is necessary that the position sensor be registered with respect to the location of interest in the anatomical body.

Figure 8:
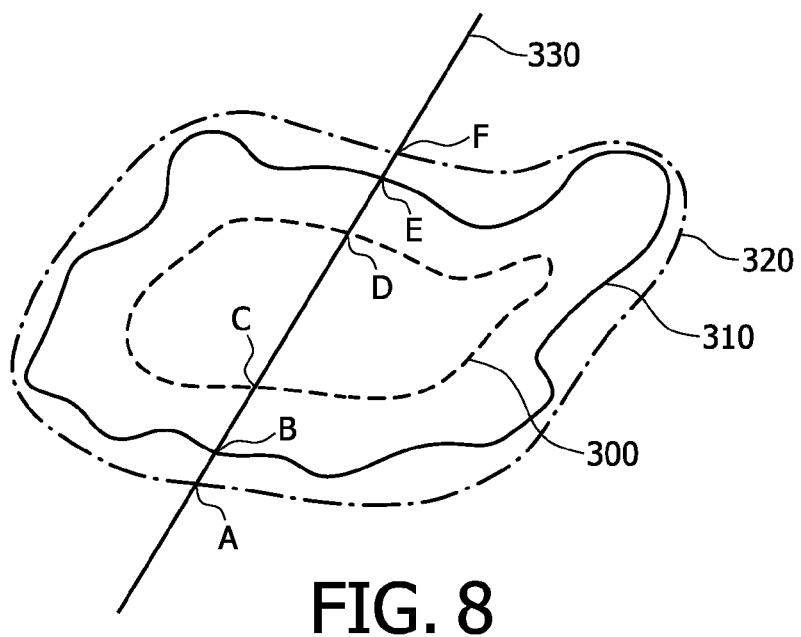
FIG. 8: tumor boundary determination.

Combining the information from the pre-recorded images (X-ray, Ultrasound, MRI) with the information from the position sensor traced by means of the electromagnetic tracking system, and the optical information from the analyze device, will lead to a better determination of the boundaries of, for example, malign tissue. As illustrated in FIG. 8, the boundary 310 deduced from the optical information (along a line 330 resulting in boundary points B and E) is in general larger than the boundary 300 of the x-ray (resulting in cross section points C and D with line 330) because of the higher sensitivity of the method. The scale factor deduced from this is used to extend the area according to that of the x-ray. The newly deduced enlarged boundary 320 will be a better estimate for the tumor boundary that can be used by the surgeon to plan the intervention.

A further embodiment is where the invention is used to guide the needle to the location of the suspicious tissue, but instead of taking a biopsy the hollow needle is used to position a localization wire. This localization wire is then used by the surgeon to find the location of the tumor to be resected.

To summarize the invention:

The current techniques used for advancement of biopsy needles in the interventional procedures are considered to be unsatisfactory and may occasionally cause harm to the patient. There are drawbacks of the current technique: accurate advancement of the needles from the incision to the lesion spot and accurate placement of the needle tip inside the lesion to be investigated. To solve this problem a biopsy guidance system is provided based on the position sensor device that transmits a signal that is indicative of its position with respect of a field generator combined with a photonic biopsy needle. This new system combines guided needle advancement with an interactive direct tissue assessment while performing biopsy procedure. In addition to that, the system enables to extend the molecular assessment of the tissue beyond the biopsy point resulting for instance in an accurate delineation of the tumor boundaries.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 light source
10 detector
22 spectrograph
24 CCD-camera
30 excitation fiber
40 collection fiber
50 lens
100, 200 biopsy device
101, 102, 103 fiber entrance position
101', 102', 103' fiber exit position
210 shaft
220 fiber
240 needle
300, 310, 320 boundary
330 optical information line
400 tracking device
402 console
410 field generator
420 system control unit
430 user supply workstation
440 sensor interface unit
450 position sensor

The invention claimed is:

1. A system for integrated guidance for positioning a biopsy device in a body, the system comprising:
   a tracking device for coarse guidance of the biopsy device to a biopsy location in the body; and
   an analyze device for fine guidance of the biopsy device to the biopsy location in the body, wherein the fine guidance is a final precise guidance to the biopsy location more precise than the coarse guidance being an initial guidance to the biopsy location, the analyze device comprising an optical detector configured to detect structures of tissues of the body for providing visible images of the structures, and a console configured to perform a spectroscopy to obtain spectral light distributions of the tissues, wherein the visible images from the optical detector include optically obtained image boundaries of the different tissues, wherein the console and the optical detector are connected to each other, wherein the analyze device is configured to provide information for discriminating different tissues including the optically obtained image boundaries of the different tissues of the body from each other based on the visible images of the structures of the tissues combined with the spectral light distributions of the tissues;

a processor configured to combine the information for discriminating the different tissues including the optically obtained image boundaries of the different tissues obtained by the analyze device with non-invasive image-determined boundaries from an image of a non-invasive imaging device providing images of the structures to calculate a scale factor between the optically obtained image boundaries and the non-invasive image-determined boundaries, and using the scale factor to enlarge the non-invasive image-determined boundaries to fully overlap the optically obtained image boundaries to obtain new boundaries of a region of interest; and the biopsy device comprising an elongate element and a tip portion, wherein the biopsy device is configured to be traced by the tracking device, wherein the optical detector is integrated in the tip portion of the biopsy device.

2. The system as claimed in claim 1, wherein the biopsy device is a biopsy needle including a needle base, a needle head and optical fibers without having a lumen, the needle base receiving the optical fibers that extend into the needle head to fiber exit positions at circumferential surface positions of the needle head.

3. The system of claim 2, wherein a first optical fiber of the optical fibers is configured to provide the fine guidance to the region of interest, and a second optical fiber of the optical fibers is configured to provide optical inspection of a portion of the region of interest harvested by the biopsy device.

4. The system of claim 3, wherein the first optical fiber ends at a front surface of the biopsy device and the second optical fiber ends at a side surface of the biopsy device, and wherein the front surface is transverse to side surface.

5. The system of claim 3, further comprising a motor for moving the second optical fiber for scanning the region of interest.

6. The system as claimed in claim 1, wherein the biopsy device comprises a hollow shaft configured to receive a needle for taking a tissue sample.

7. The system as claimed in claim 1, wherein the biopsy device comprises a position sensor configured to transmit a signal to the tracking device, wherein the signal includes position information indicative of a position of the biopsy device relative to body structures.

8. The system as claimed in claim 7, wherein the tracking device is configured to link the position information to the image of the imaging device.

9. The system as claimed in claim 8, wherein the information provided by the analyze device is registered in the image of the imaging device, making use of the position information.

10. The system as claimed in claim 1, wherein the optical detector of the analyze device comprises an optical fiber.

11. The system as claimed in claim 1, wherein the spectroscopy is selected from one of a group consisting of differential path length spectroscopy, Raman spectroscopy, optical coherence tomography, and light scattering spectroscopy.

12. The system as claimed in claim 1, wherein the tracking device is a non-invasive tracking modality based on an electromagnetic field.

13. The system of claim 1, wherein the optical detector is configured to provide cellular imaging with micron resolution allowing cellular structures of the structures to become visible, and wherein the processor is configured to combine the cellular imaging with spectroscopy performed by the console for tissue characterization without using staining.

14. A biopsy device comprising:

a position sensor configured to provide information indicative of a position of the biopsy device for providing a coarse guidance of the biopsy device to a biopsy location in a body;

an optical fiber integrated in a tip portion of the biopsy device and configured to emit and receive light for providing a fine guidance of the biopsy device to the biopsy location in the body, wherein the fine guidance is a final precise guidance to the biopsy location more precise than the coarse guidance being an initial guidance to the biopsy location; and an analyze device for the fine guidance of the biopsy device to the biopsy location in the body, the analyze device comprising an optical detector configured to detect structures of tissues of the body for providing visible images of the structures, and a console configured to perform a spectroscopy to obtain spectral light distributions of the tissues, wherein the visible images from the optical detector include optically obtained image boundaries of the different tissues, wherein the console and the optical detector are connected to each other, wherein the analyze device is configured to provide information for discriminating different tissues including the optically obtained image boundaries of the different tissues of the body from each other based on the visible images of the structures of the tissues combined with the spectral light distributions of the tissues; and a processor configured to combine the information for discriminating the different tissues including the optically obtained image boundaries of the different tissues obtained by the analyze device with non-invasive image-determined boundaries from an image of an imaging device providing images of the structures to calculate a scale factor between the optically obtained image boundaries and the non-invasive image-determined boundaries, and using the scale factor to enlarge the non-invasive image-determined boundaries to fully overlap the optically obtained image boundaries to obtain new boundaries of a region of interest.

15. The biopsy device as claimed in claim 14, wherein the biopsy device is a biopsy needle including a needle base, a needle head and optical fibers without having a lumen, the needle base receiving the optical fibers that extend into the needle head to fiber exit positions at circumferential surface positions of the needle head.

16. The biopsy device as claimed in claim 14, wherein the biopsy device comprises a hollow shaft configured to receive a needle for taking a tissue sample.

17. The biopsy device of claim 14, further comprising a further optical fiber ending at a side portion of the biopsy device, wherein the side portion is transverse to the tip portion, and wherein the further optical fiber is configured to provide optical inspection of a portion of the region of interest harvested by the biopsy device.

18. The biopsy device of claim 14, wherein the optical detector is configured to provide cellular imaging with micron resolution allowing cellular structures of the structures to become visible, and wherein the processor is configured to combine the cellular imaging with spectroscopy performed by the console for tissue characterization without using staining.

19. A method of positioning a biopsy device in a body, the method comprising the acts of:

introducing the biopsy device into the body, the biopsy device comprising an optical fiber integrated in a tip of the biopsy device and configured to emit and receive light;

tracing the biopsy device in the body by a non-invasive electromagnetic tracking device for providing a coarse guidance of the biopsy device to a biopsy location in the body;

fine positioning the biopsy device assisted by an analyze device included in the biopsy device, the analyze device comprising the optical fiber device for providing a fine guidance of the biopsy device to the biopsy location in the body, wherein the fine guidance is a final precise guidance to the biopsy location more precise than the coarse guidance being an initial guidance to the biopsy location, the analyze device further comprising an optical detector configured to detect structures of tissues of the body for providing visible images of the structures, wherein the visible images from the optical detector include optically obtained image boundaries of the different tissues;

obtaining by a console spectroscopy optical information including spectral light distributions of the tissues;

discriminating different tissues including the optically obtained image boundaries of the different tissues in front of the tip of the biopsy device from information provided by the analyze device based on the visible images of the structures of the tissues combined with the spectral light distributions of the tissues; and combining the information for discriminating the different tissues including the optically obtained image boundaries of the different tissues obtained by the analyze device with non-invasive image-determined boundaries from an image of an imaging device providing images of the structures to calculate a scale factor between the optically obtained image boundaries and the non-invasive image-determined boundaries, and using the scale factor to enlarge the non-invasive image-determined boundaries to fully overlap the optically obtained image boundaries to obtain new boundaries of a region of interest.

20. The method of claim 19, wherein the optical detector is configured to provide cellular imaging with micron resolution allowing cellular structures of the structures to become visible, and wherein the processor is configured to combine the cellular imaging with spectroscopy performed by the console for tissue characterization without using staining.

* * * * *